(12) United States Patent
Gant et al.

(10) Patent No.: US 6,380,214 B1
(45) Date of Patent: Apr. 30, 2002

(54) HETEROCYCLIC DERIVATIVES USEFUL AS ANTICANCER AGENTS

(75) Inventors: Thomas George Gant, Niantic; Mark Carl Noe, Mystic, both of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/549,893

(22) Filed: Apr. 17, 2000

Related U.S. Application Data

(60) Provisional application No. 60/134,933, filed on May 19, 1999.

(51) Int. Cl.$^7$ .................. A61K 31/381; A61K 31/4436; A61K 31/425; C07D 275/03; C07D 333/36; C07D 417/12
(52) U.S. Cl. .................. 514/314; 514/342; 514/372; 514/445; 514/407; 546/172; 546/175; 546/281.4; 548/213; 548/214; 548/368.4; 549/63
(58) Field of Search ................... 549/63; 546/172, 546/175, 281.4; 548/213, 214; 514/445, 314, 372, 342

(56) References Cited

U.S. PATENT DOCUMENTS

| 4,057,416 A | * | 11/1977 | Gibbons | 71/90 |
| 4,075,001 A | * | 2/1978 | Gibbons | 71/90 |
| 4,760,063 A | * | 7/1988 | Hallenbach | 514/230.5 |
| 4,859,699 A | * | 8/1989 | Carney | 514/447 |
| 5,538,939 A | * | 7/1996 | Muenster | 504/269 |
| 6,037,340 A | * | 3/2000 | Castelhano | 514/183 |

FOREIGN PATENT DOCUMENTS

| CA | 1323365 | * | 10/1993 |
| DE | 1950990 | * | 5/1970 |
| DE | 2408234 | * | 9/1975 |
| DE | 3529247 | * | 11/1986 |
| DE | 3541631 | * | 5/1987 |
| EP | 640606 | * | 3/1995 |
| FR | 2132691 | * | 11/1972 |
| WO | 9521613 |   | 8/1995 |
| WO | 9622991 | * | 8/1996 |

OTHER PUBLICATIONS

King FD. Medicinal Chemistry. Principles and Practice. The Royal Society of Chemistry. Pp. 206–208, 1994.*
So'fina, Goldin and Belousova. National Cancer Institute Monograph 55. NIH Publication No. 80–1933, Dec. 1980.*

* cited by examiner

*Primary Examiner*—Evelyn Mei Huang
(74) *Attorney, Agent, or Firm*—Peter C. Richardson; Paul H. Ginsburg; Jeffrey N. Myers

(57) ABSTRACT

The present invention relates to compounds of the formula 1

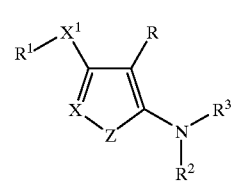

and to pharmaceutically acceptable salts, prodrugs and solvates thereof, wherein Z, X, $X^1$, $R^1$, $R^2$ and $R^3$ are as defined herein as it relates to pharmaceutical compositions containing the above compounds for the treatment of disorders mediated by angiogenesis in mammals by administration of the above compounds.

2 Claims, No Drawings

HETEROCYCLIC DERIVATIVES USEFUL AS ANTICANCER AGENTS

This application claims the benefit of priority of U.S. Provisional Application Ser. No. 60/134,933, filed on May 19, 1999.

BACKGROUND OF THE INVENTION

This invention relates to novel isothiazole derivatives that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

It is known that a cell may become cancerous by virtue of the transformation of a portion of its DNA into an oncogene (i.e. a gene that upon activation leads to the formation of malignant tumor cells). Many oncogenes encode proteins which are aberrant tyrosine kinases capable of causing cell transformation. Alternatively, the overexpression of a normal proto-oncogenic tyrosine kinase may also result in proliferative disorders, sometimes resulting in a malignant phenotype. It has been shown that certain tyrosine kinases may be mutated or overexpressed in many human cancers such as brain, lung, squamous cell, bladder, gastric, breast, head and neck, oesophageal, gynecological and thyroid cancers. Furthermore, the overexpression of a ligand for a tyrosine kinase receptor may result in an increase in the activation state of the receptor, resulting in proliferation of the tumor cells or endothelial cells. Thus, it is believed that inhibitors of receptor tyrosine kinases, such as the compounds of the present invention, are useful as selective inhibitors of the growth of mammalian cancer cells.

It is known that polypeptide growth factors, such as vascular endothelial growth factor (VEGF) having a high affinity to the human kinase insert-domain-containing receptor (KDR) or the murine fetal liver kinase 1 (FLK-1) receptor, have been associated with the proliferation of endothelial cells and more particularly vasculogenesis and angiogenesis. See PCT international application publication number WO 95/21613 (published Aug. 17, 1995). Agents, such as the compounds of the present invention, that are capable of binding to or modulating the KDR/FLK-1 receptor may be used to treat disorders related to vasculogenesis or angiogenesis such as diabetes, diabetic retinopathy, hemangioma, glioma, melanoma, Kaposi's sarcoma and ovarian, breast, lung, pancreatic, prostate, colon and epidermoid cancer. Isothiazole derivatives useful in the treatment of hyperproliferative disorders are referred to in U.S. provisional application No. 60/087,963, filed Jun. 4, 1998, which is incorporated herein by reference in its entirety.

SUMMARY OF THE INVENTION

The present invention relates to compounds of the formula 1

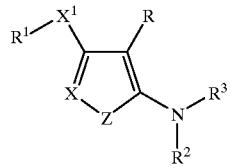

and to pharmaceutically acceptable salts, prodrugs and solvates thereof, wherein:

Z is S, O, or $NR^6$;

X is N or $CR^4$;

$X^1$ is O, S, SO, $SO_2$, $NR^6$, or $CR^5R^6$;

R is $—CONR^5R^6$, $—CO_2R^5$, $—NR^5R^6$, $—NR^5SO_2R^6$, $—SO_2NR^5R^6$, $—NR^6C(O)R^5$ or an $C_6–C_{10}$ aryl or 4–10 membered heterocyclic group containing 1–4 heteroatoms from the group N, O, S, or $SO_2$;

$R^1$ is H, $C_1–C_{10}$ alkyl, $C_2–C_{10}$ alkenyl, $C_2–C_{10}$ alkynyl, $—(CH_2)_t(C_6–C_{10}$ aryl), or $—(CH_2)_t(4–10$ membered heterocyclic), wherein t is an integer from 0 to 5; said alkyl group optionally includes 1 or 2 hetero moieties selected from O, S and $—N(R^5)—$ with the proviso that two O atoms, two S atoms, or an O and S atom are not attached directly to each other; said aryl and heterocyclic $R^1$ groups are optionally fused to a $C_6–C_{10}$ aryl group, a $C_5–C_8$ saturated cyclic group, or a 4–10 membered heterocyclic group; 1 or 2 carbon atoms in the foregoing heterocyclic moieties are optionally substituted by an oxo (=O) moiety; the $—(CH_2)_t—$ moieties of the foregoing $R^1$ groups optionally include a carbon-carbon double or triple bond where t is an integer from 2 to 5, and the foregoing $R^1$ groups other than H are optionally substituted by 1 to 5 $R^8$ groups;

$R^2$ is H, $C_1–C_{10}$ alkyl, $C_2–C_{10}$ alkenyl, $C_2–C_{10}$ alkynyl, $—C(O)(C_1–C_{10}$ alkyl), $—(CH_2)_t(C_6–C_{10}$ aryl), $—(CH_2)_t(4–10$ membered heterocyclic), $—C(O)(CH_2)_t(C_6–C_{10}$ aryl), or $—C(O)(CH_2)_t(4–10$ membered heterocyclic), wherein t is an integer from 0 to 5; said alkyl group optionally includes 1 or 2 hetero moieties selected from O, S and $—N(R^6)—$ with the proviso that two O atoms, two S atoms, or an O and S atom are not attached directly to each other; said aryl and heterocyclic $R^1$ groups are optionally fused to a $C_6–C_{10}$ aryl group, a $C_5–C_8$ saturated cyclic group, or a 4–10 membered heterocyclic group; 1 or 2 carbon atoms in the foregoing heterocyclic moieties are optionally substituted by an oxo (=O) moiety; the $—(CH_2)_t—$ moieties of the foregoing $R^1$ groups optionally include a carbon-carbon double or triple bond where t is an integer from 2 to 5; and the foregoing $R^1$ groups, except H, are optionally substituted by 1 to 5 $R^8$ groups;

$R^3$ is $—CR^5R^6R^7$, $SO_2R^5$, or $—CONR^5R^6$;

$R^4$ is H or $C_1–C_6$ alkyl and may be taken together with $X^1$ or $R^1$ to form a 5 to 6 membered saturated ring or a 5 to 6 membered heteroaryl ring, wherein said saturated and heteroaryl rings optionally include 1 to 3 heteroatoms in addition to $X^1$, selected from O, S and $—N(R^6)$, where said $—N(R^6)—$ is optionally =N— or —N=, said saturated ring optionally may be partially unsaturated by including 1 or 2 carbon-carbon double bonds, and said saturated and heteroaryl rings, including the $R^6$ group of said $—N(R^6)—$, are optionally substituted by 1 to 5 $R^8$ groups;

each $R^5$ is independently H, $C_1–C_{10}$ alkyl, $C_2–C_{10}$ alkenyl, $C_2–C_{10}$ alkynyl, $—C(O)(C_1–C_{10}$ alkyl), —(CH$_2$)$_t$(C$_6$–C$_{10}$ aryl), —(CH$_2$)$_t$(4–10 membered heterocyclic), —C(O)(CH$_2$)$_t$(C$_6$–C$_{10}$ aryl), or —C(O)(CH$_2$)$_t$(4–10 membered heterocyclic), wherein t is an integer from 0 to 5; said alkyl group optionally includes 1 or 2 hetero moieties selected from O, S and —N(R$^6$)— with the proviso that two O atoms, two S atoms, or an O and S atom are not attached directly to each other; said aryl and heterocyclic R$^1$ groups are optionally fused to a C$_6$–C$_{10}$ aryl group, a C$_5$–C$_8$ saturated cyclic group, or a 5–10 membered heterocyclic group; 1 or 2 carbon atoms in the foregoing heterocyclic moieties are optionally substituted by an oxo (=O) moiety; the —(CH$_2$)$_t$— moieties of the foregoing R$^1$ groups optionally include a carbon-carbon double or triple bond where t is an integer from 2 to 5; and the foregoing R$^5$ groups, except H, are optionally substituted by 1 to 5 R$^8$ groups;

each R$^6$ is independently selected from the list of substituents provided in the definition of R$^5$, —SO$_2$(CH$_2$)$_t$(C$_6$–C$_{10}$ aryl), —SO$_2$(CH$_2$)$_t$(4–10 membered heterocyclic), and —OR$^5$, t is an integer from 0 to 5, the —(CH$_2$)$_t$— moieties of the foregoing R$^2$ groups optionally include a carbon-carbon double or triple bond where t is an integer from 2 to 5, and the foregoing R$^6$ groups are optionally substituted by 1 to 5 R$^8$ groups;

each R$^7$ is independently H, C$_1$–C$_{10}$ alkyl, C$_2$–C$_{10}$ alkenyl, C$_2$–C$_{10}$ alkynyl, —C(O)(C$_1$–C$_{10}$ alkyl), —(CH$_2$)$_t$(C$_6$–C$_{10}$ aryl), —(CH$_2$)$_t$(4–10 membered heterocyclic), —C(O)(CH$_2$)$_t$(C$_6$–C$_{10}$ aryl), or —C(O)(CH$_2$)$_t$(4–10 membered heterocyclic), wherein t is an integer from 0 to 5; said alkyl group optionally includes 1 or 2 hetero moieties selected from O, S and —N(R$^6$)— with the proviso that two O atoms, two S atoms, or an O and S atom are not attached directly to each other; said aryl and heterocyclic R$^1$ groups are optionally fused to a C$_6$–C$_{10}$ aryl group, a C$_5$–C$_8$ saturated cyclic group, or a 4–10 membered heterocyclic group; 1 or 2 carbon atoms in the foregoing heterocyclic moieties are optionally substituted by an oxo (=O) moiety; the —(CH$_2$)$_t$— moieties of the foregoing R$^1$ groups optionally include a carbon-carbon double or triple bond where t is an integer from 2 to 5; and the foregoing R$^7$ groups, except H, are optionally substituted by 1 to 5 R$^8$ groups;

or R$^5$ and R$^6$ may be taken together with the nitrogen to which each is attached to form a 4–10 membered saturated monocyclic or polycyclic ring or a 5–10 membered heteroaryl ring, wherein said saturated and heteroaryl rings optionally include 1 or 2 heteroatoms selected from O, S and —N(R$^6$)— in addition to the nitrogen to which R$^5$ and R$^6$ are attached, said —N(R$^6$)— is optionally =N— or —N= where R$^5$ and R$^6$ are taken together as said heteroaryl group, said saturated ring optionally may be partially unsaturated by including 1 or 2 carbon-carbon double bonds, and said saturated and heteroaryl rings, including the R$^6$ group of said —N(R$^6$)—, are optionally substituted by 1 to 5 R$^8$ groups;

each R$^8$ is independently selected from H, C$_1$–C$_{10}$ alkyl, C$_2$–C$_{10}$ alkenyl, C$_2$–C$_{10}$ alkynyl, halo, cyano, nitro, trifluoromethyl, trifluoromethoxy, azido, —OR$^5$, —C(O)R$^5$, —C(O)OR$^5$, —NR$^6$C(O)OR$^5$, —OC(O)R$^5$, —NR$^6$SO$_2$R$^5$, —SO$_2$NR$^5$R$^6$, —NR$^6$C(O)R$^5$, —C(O)NR$^5$R$^6$, —NR$^5$R$^6$, —S(O)$_j$R$^7$ wherein j is an integer from 0 to 2, —SO$_3$H, —NR$^5$(CR$^6$R$^7$)$_t$OR$^6$, —(CH$_2$)$_t$(C$_6$–C$_{10}$ aryl), —SO$_2$(CH$_2$)$_t$(C$_6$–C$_{10}$ aryl), —S(CH$_2$)$_t$(C$_6$–C$_{10}$ aryl), —O(CH$_2$)$_t$(C$_6$–C$_{10}$ aryl), —(CH$_2$)$_t$(4–10 membered heterocyclic), and —(CR$^6$R$^7$)$_m$OR$^6$, wherein m is an integer from 1 to 5 and t is an integer from 0 to 5; said alkyl group optionally contains 1 or 2 hetero moieties selected from O, S and —N(R$^6$)— with the proviso that two O atoms, two S atoms, or an O and S atom are not attached directly to each other; said aryl and heterocyclic R$^4$ groups are optionally fused to a C$_6$–C$_{10}$ aryl group, a C$_5$–C$_8$ saturated cyclic group, or a 4–10 membered heterocyclic group; 1 or 2 carbon atoms in the foregoing heterocyclic moieties are optionally substituted by an oxo (=O) moiety; and the alkyl, aryl and heterocyclic moieties of the foregoing R$^8$ groups are optionally substituted by 1 to 5 substituents independently selected from halo, cyano, nitro, trifluoromethyl, trifluoromethoxy, azido, —NR$^{10}$SO$_2$R$^9$, —SO$_2$NR$^9$R$^{10}$, —C(O)R$^9$, —C(O)OR$^9$, —OC(O)R$^9$, —NR$^{10}$C(O)R$^9$, —C(O)NR$^9$R$^{10}$, —NR$^9$R$^{10}$, —(CR$^{10}$R$^7$)$_m$OR$^{10}$ wherein m is an integer from 1 to 5, and R$^9$ and R$^{10}$ are each defined as H, C$_1$–C$_6$ alkyl, —(CH$_2$)t(C$_6$–C$_{10}$ aryl) or —(CH$_2$)t(4–10 membered heterocyclic) and t is an integer from 0 to 5.

Compounds excluded from the present invention include those wherein all of the following conditions are met simultaneously: Z is S; and X$^1$ is O or S; and X is N; and R is CONH$_2$; and R$^2$ is H; and R$^3$ is CONR$^5$R$^6$.

Preferred compounds include those of formula 1 wherein Z=S and wherein R$^1$ is C$_1$–C$_{10}$ alkyl, C$_2$–C$_{10}$ alkenyl, C$_2$–C$_{10}$ alkynyl, —(CH$_2$)$_t$(C$_6$–C$_{10}$ aryl), or —(CH$_2$)$_t$(4–10 membered heterocyclic), wherein t is an integer from 0 to 5 and R$^2$ is H.

Other preferred compounds include those of formula 1 wherein R$^3$ is CONR$^5$R$^6$ where R$^5$ is H and R$^6$ is —(CH$_2$)$_t$(4–10 membered heterocyclic), wherein t is an integer from 0 to 6; said heterocyclic group is optionally fused to a C$_6$–C$_{10}$ aryl group, a C$_5$–C$_8$ saturated cyclic group, or a 4–10 membered heterocyclic group; and said R$^6$ group, including the optionally fused portions of said R$^6$ group, is optionally substituted by 1 or 2 substituents independently selected from C$_1$–C$_4$ alkyl, hydroxy and hydroxymethyl. Specific preferred heterocyclic groups of said R$^6$ group are morpholino, pyrrolidinyl, imidazolyl, piperazinyl, piperidinyl, and 2,5-diazabicyclo[2.2.1]hept-2-yl, the t variable of said R$^6$ group ranges from 2 to 6, and said heterocyclic groups are optionally substituted by hydroxy, hydroxymethyl and methyl.

Specific embodiments of the present invention include the following compounds:

2-(3,3-Dimethyl-ureido)-4-propoxy-thiophene-3-carboxylic acid amide;

4-Butoxy-2-(3,3-dimethyl-ureido)-thiophene-3-carboxylic acid amide;

2-(3,3-Dimethyl-ureido)-4-pentyloxy-thiophene-3-carboxylic acid amide;

2-(3,3-Dimethyl-ureido)-4-hexyloxy-thiophene-3-carboxylic acid amide;

2-(3,3-Dimethyl-ureido)-4-heptyloxy-thiophene-3-carboxylic acid amide;

4-Benzylsulfanyl-2-(3,3-dimethyl-ureido)-thiophene-3-carboxylic acid amide;

2-(3,3-Dimethyl-ureido)-4-hexylsulfanyl-thiophene-3-carboxylic acid amide;

2-(3,3-Dimethyl-ureido)-4-pentylsulfanyl-thiophene-3-carboxylic acid amide;

2-(3,3-Dimethyl-ureido)-4-phenethylsulfanyl-thiophene-3-carboxylic acid amide;

2-(3,3-Dimethyl-ureido)-4-(pyridin-2-ylmethylsulfanyl)-thiophene-3-carboxylic acid amide;
2-(3,3-Dimethyl-ureido)-4-(naphthalen-1-ylmethylsulfanyl)-thiophene-3-carboxylic acid amide;
2-(3,3-Dimethyl-ureido)-4-(naphthalen-2-ylmethylsulfanyl)-thiophene-3-carboxylic acid amide;
2-(3,3-Dimethyl-ureido)-4-(quinolin-2-ylmethylsulfanyl)-thiophene-3-carboxylic acid amide
4-(4-Chloro-benzylsulfanyl)-2-(3,3-dimethyl-ureido)-thiophene-3-carboxylic acid amide;
2-(3,3-Dimethyl-ureido)-4-(1-phenyl-ethylsulfanyl)-thiophene-3-carboxylic acid amide
4-(2-Chloro-benzylsulfanyl)-2-(3,3-dimethyl-ureido)-thiophene-3-carboxylic acid amide
4-(3-Chloro-benzylsulfanyl)-2-(3,3-dimethyl-ureido)-thiophene-3-carboxylic acid amide
2-(3,3-Dimethyl-ureido)-4-(4-methyl-benzylsulfanyl)-thiophene-3-carboxylic acid amide;
2-(3,3-Dimethyl-ureido)-4-(4-methoxy-benzylsulfanyl)-thiophene-3-carboxylic acid amide;
2-(3,3-Dimethyl-ureido)-4-(4-vinyl-benzylsulfanyl)-thiophene-3-carboxylic acid amide;
2-(3,3-Dimethyl-ureido)-4-(4-trifluoromethyl-benzylsulfanyl)-thiophene-3-carboxylic acid amide;
2-(3,3-Dimethyl-ureido)-4-(pyridin-4-ylmethylsulfanyl)-thiophene-3-carboxylic acid amide;
2-(3,3-Dimethyl-ureido)-4-(pyridin-3-ylmethylsulfanyl)-thiophene-3-carboxylic acid amide;
5-Acetylamino-3-pentylsulfanyl-isothiazole-4-carboxylic acid amide;
5-Benzoylamino-3-pentylsulfanyl-isothiazole-4-carboxylic acid amide;
1-Methyl-3-[3-pentylsulfanyl-4-(1H-tetrazol-5-yl)-isothiazol-5-yl]-urea;
5-(3-Methyl-ureido)-3-pentylsulfanyl-isothiazole-4-carboxylic acid;
5-Amino-3-pentylsulfanyl-pyrazole-1,4-dicarboxylic acid 4-amide 1-methylamide;
5-Amino-3-pentylsulfanyl-pyrazole-1,4-dicarboxylic acid 4-amide 1-dimethylamide;
5-(3,3-Dimethyl-ureido)-3-pentylsulfanyl-1H-pyrazole-4-carboxylic acid amide;
5-Acetylamino-3-pentylsulfanyl-1H-pyrazole-4-carboxylic acid amide;
5-Benzoylamino-3-pentylsulfanyl-1H-pyrazole-4-carboxylic acid amide;
5-Amino-1-benzoyl-3-pentylsulfanyl-1H-pyrazole-4-carboxylic acid amide;

and the pharmaceutically acceptable salts and hydrates of the foregoing compounds.

The invention also relates to a pharmaceutical composition for the treatment of a hyperproliferative disorder in a mammal which comprises a therapeutically effective amount of a compound of formula 1, or a pharmaceutically acceptable salt or hydrate thereof, and a pharmaceutically acceptable carrier. In one embodiment, said pharmaceutical composition is for the treatment of cancer such as brain, lung, squamous cell, bladder, gastric, pancreatic, breast, head, neck, renal, prostate, colorectal, oesophageal, gynecological (such as ovarian) or thyroid cancer. In another embodiment, said pharmaceutical composition is for the treatment of a non-cancerous hyperproliferative disorder such as benign hyperplasia of the skin (e.g., psoriasis) or prostate (e.g., benign prostatic hypertropy (BPH)).

The invention also relates to a pharmaceutical composition for the treatment of pancreatitis or kidney disease (including proliferative glomerulonephritis and diabetes-induced renal disease) in a mammal which comprises a therapeutically effective amount of a compound of formula 1, or a pharmaceutically acceptable salt or hydrate thereof, and a pharmaceutically acceptable carrier.

The invention also relates to a pharmaceutical composition for the prevention of blastocyte implantation in a mammal which comprises a therapeutically effective amount of a compound of formula 1, or a pharmaceutically acceptable salt or hydrate thereof, and a pharmaceutically acceptable carrier.

The invention also relates to a pharmaceutical composition for treating a disease related to vasculogenesis or angiogenesis in a mammal which comprises a therapeutically effective amount of a compound of formula 1, or a pharmaceutically acceptable salt or hydrate thereof, and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal which comprises administering to said mammal a therapeutically effective amount of the compound of formula 1, or a pharmaceutically acceptable salt or hydrate thereof. In one embodiment, said method relates to the treatment of cancer such as brain, squamous cell, bladder, gastric, pancreatic, breast, head, neck, oesophageal, prostate, colorectal, lung, renal, gynecological (such as ovarian) or thyroid cancer. In another embodiment, said method relates to the treatment of a non-cancerous hyperproliferative disorder such as benign hyperplasia of the skin (e.g., psoriasis) or prostate (e.g., benign prostatic hypertropy (BPH)).

The invention also relates to a method for the treatment of a hyperproliferative disorder in a mammal which comprises administering to said mammal a therapeutically effective amount of a compound of formula 1, or a pharmaceutically acceptable salt or hydrate thereof, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The invention also relates to a method of treating pancreatitis or kidney disease in a mammal which comprises administering to said mammal a therapeutically effective amount of a compound of formula 1, or a pharmaceutically acceptable salt or hydrate thereof.

The invention also relates to a method of preventing blastocyte implantation in a mammal which comprises administering to said mammal a therapeutically effective amount of a compound of formula 1, or a pharmaceutically acceptable salt or hydrate thereof.

The invention also relates to a method of treating diseases related to vasculogenesis or angiogenesis in a mammal which comprises administering to said mammal an effective amount of a compound of formula 1, or a pharmaceutically acceptable salt or hydrate thereof. In one embodiment, said method is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with the compounds of formulas 1, and the pharmaceutically acceptable salts and hydrates of said compounds, according to the methods of this invention include, for example, patients that have been diagnosed as having psoriasis, BPH, lung cancer, bone cancer, pancreatic cancer, skin cancer, cancer of the head and neck, cutaneous or intraocular melanoma, uterine cancer, ovarian cancer, rectal cancer or cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

The term "halo", as used herein, unless otherwise indicated, includes fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties. It is understood that for cyclic moieties at least three carbon atoms are required in said alkyl group.

The term "alkenyl", as used herein, unless otherwise indicated, includes monovalent hydrocarbon radicals having at least one carbon-carbon double bond and also having straight, cyclic or branched moieties as provided above in the definition of "alkyl".

The term "alkynyl", as used herein, unless otherwise indicated, includes monovalent hydrocarbon radicals having at least one carbon-carbon triple bond and also having straight, cyclic or branched moieties as provided above in the definition of "alkyl".

The term "alkoxy", as used herein, unless otherwise indicated, includes O-alkyl groups wherein "alkyl" is as defined above.

The term "aryl", as used herein, unless otherwise indicated, includes an organic radical derived from an aromatic hydrocarbon by removal of one hydrogen, such as phenyl or naphthyl.

The term "4–10 membered heterocyclic", as used herein, unless otherwise indicated, includes aromatic and non-aromatic heterocyclic groups containing one or more heteroatoms each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The phrase "pharmaceutically acceptable salt(s)", as used herein, unless otherwise indicated, includes salts of acidic or basic groups which may be present in the compounds of formula 1. The compounds of formula 1 that are basic in nature are capable of forming a wide variety of salts with various inorganic and organic acids. The acids that may be used to prepare pharmaceutically acceptable acid addition salts of such basic compounds of formula 1 are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the formula 1 that are acidic in nature, are capable of forming base salts with various pharmacologically acceptable cations. Examples of such salts include the alkali metal or alkaline earth metal salts and particularly, the sodium and potassium salts.

The subject invention also includes isotopically-labelled compounds, and the pharmaceutically acceptable salts thereof, which are identical to those recited in formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula 1 of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing and methods of treating bacterial infections through administering prodrugs of compounds of the formula 1. Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. The amide and ester moieties may incorporate groups including but not limited to ether, amine and carboxylic acid functionalities. Free hydroxy groups may be derivatized using groups including but not limited to hemisuccinates, phosphate esters, dimethylaminoacetates, and phosphoryloxymethyloxycarbonyls, as outlined in D. Fleisher, R. Bong, B. H. Stewart, Advanced Drug Delivery Reviews (1996) 19, 115. Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., J. Medicinal Chemistry (1996) 39, 10.

Certain compounds of formula 1 may have asymmetric centers and therefore exist in different enantiomeric forms. This invention relates to the use of all optical isomers and stereoisomers of the compounds of formula 1 and mixtures thereof. The compounds of formula 1 may also exist as tautomers. This invention relates to the use of all such tautomers and mixtures thereof.

DETAILED DESCRIPTION OF THE INVENTION

Compounds of the formula 1 and their pharmaceutically acceptable salts and solvates may be prepared as referenced:

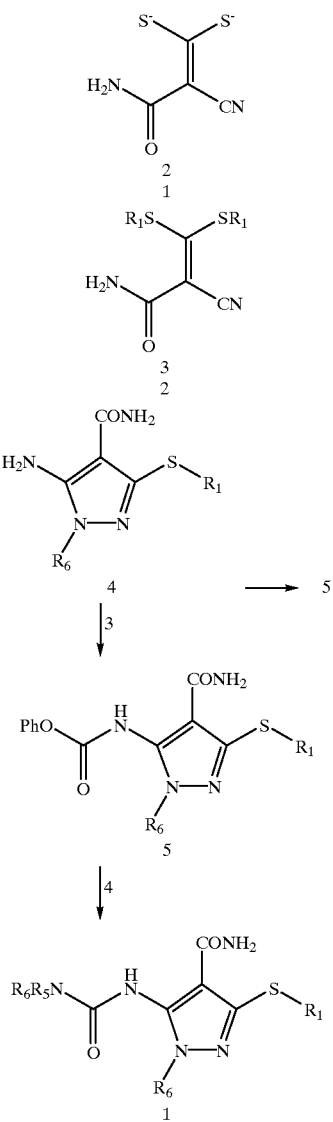

Scheme 1 illustrates the condensation of a potassium salt of 2-cyano-3,3-dimercapto-acrylamide with an $R^1$ containing electrophile, cyclization with an $R^6$ containing hydrazine, acylation with phenyl chloroformate and reaction with an $R^5R^6$ containing amine to give the final compound. In Step 1 of Scheme 1, the compound of formula 3 may be prepared by treating an ammonium salt of the compound of formula 2 with an $R^1$-containing alkyl bromide, iodide, mesylate or triflate in a polar aprotic solvent such as dimethylformamide at a temperature between 0° C. and 100, preferably at 70° C. for a period of time between 30 min and 24 h, preferably 1 h. In step 2 of Scheme 1, the compound of formula 4 may be prepared by treating the compound of formula 3 with between 1 and 2 equivalents, preferably 1.2 equivalents, of an $R^6$ containing hydrazine (where $R^6$ is an alkyl or aryl group) salt and between 1 and 2 equivalents, preferably 1.2 equivalents, of a suitably strong base, such as a hydroxide base, preferably potassium hydroxide, in a polar solvent, preferably and alcoholic solvent, such as methanol, at a temparature between 23° C. and 120° C., preferably 80° C. for 12 to 48 hours, preferably 24 hours. In Step 3 of Scheme 1, the compound of formula 5 may be prepared by treating a compound of formula 4 with between 1 and 10 equivalents, preferably 1 to 4 equivalents, of an arylchloroformate, preferably phenylchloroformate, in the presence of a suitably strong base, such as an aromatic amine, preferably pyridine in a polar aprotic solvent, such as an ethereal solvent, preferably THF (tetrahydrofuran) at a temperature between −10 and 80° C., for 1 to 12 hours, preferably 6 hours. In Step 4 of Scheme 1, the compound of formula 1 may be prepared by treating the compound of formula 5 with a desired amine of the formula $R^5R^6NH$ at a temperature sufficient to effect reaction, typically 0° C. to 100° C., preferably 50° C. to 70° C., for a period ranging from 1 hour to 48 hours, preferably overnight. The compound of formula 1 is then isolated.

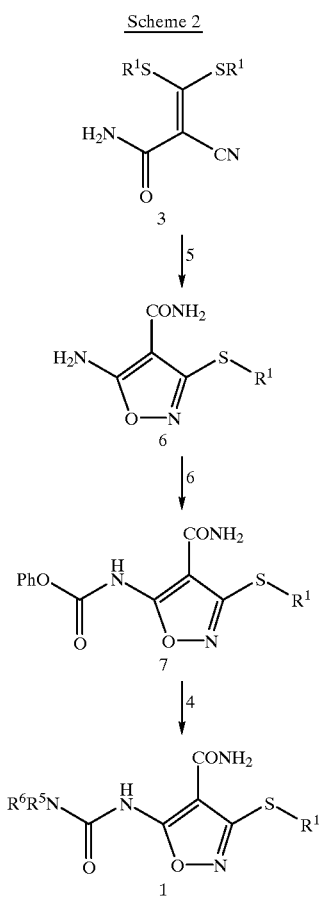

In step 1 of Scheme 2, the compound of formula 6 may be prepared by treating the compound of formula 3 with between 1 and 5 equivalents, preferably 2 equivalents, of a salt of hydroxylamine, preferably hydroxylamine hydrochloride and between 1 and 5 equivalents, preferably 2 equivalents, of a suitably strong base, such as a hydroxide base, preferably potassium hydroxide, in a polar solvent, such as water or an alcoholic solvent, prreferably water, at a temparature between 23° C. and 80° C., preferably 23°C. for 12 to 72 hours, preferably 48 hours. In Step 2 of Scheme 2, the compound of formula 7 may be prepared by treating a compound of formula 6 with between 1 and 5 equivalents, preferably 3 equivalents, of an arylchloroformate, preferably phenylchloroformate, in the presence of a suitably strong base, such as an aromatic amine, preferably pyridine in a polar aprotic solvent, such as an ethereal solvent, preferably THF at a temperature between −10 and 80° C. for 1 to 72 hours, preferably 48 hours. In Step 3 of Scheme 2, the compound of formula 1 may be prepared by treating the compound of formula 5 with a desired amine of the formula $R^5R^6NH$ at a temperature sufficient to effect reaction, typically 0° C. to 100° C., preferably 50° C. to 70° C., for a period ranging from 1 hour to 48 hours, preferably overnight. The compound of formula 1 is then isolated.

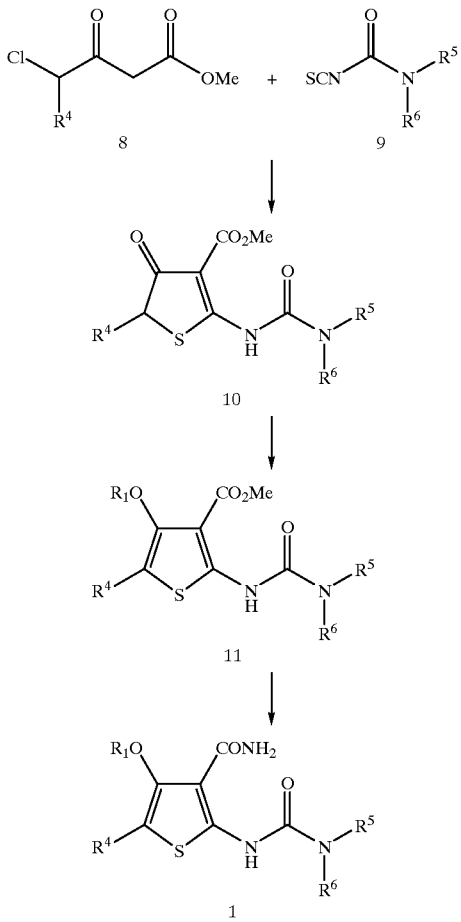

In Scheme 3, a condensation partner such as the ketoester 8 may be reacted with a suitable base such as sodium hydride in a suitable solvent such as tetrahydrofuran (THF) followed by reaction with an aminoacylisothiocyanate such as compound 9 at a temperature range between −20° C. and reflux, preferably 0° C., until reaction is complete to afford thiophenone 10. The thiophenone may then be reacted with an appropriate alcohol in a suitable solvent, such as the alcohol itself, with an appropriate amount of an appropriate catalyst, such as $H_2SO_4$ at an appropriate temperature, such as reflux, until such time as the reaction is complete to afford the thiophene 11. The amide functionality may then be installed by reaction of 11 with an ammonia source such as ammonium hydroxide in ethanol at an appropriate temperature, such as 40 C. in a sealed tube to afford the compound of formula 1.

Scheme 4

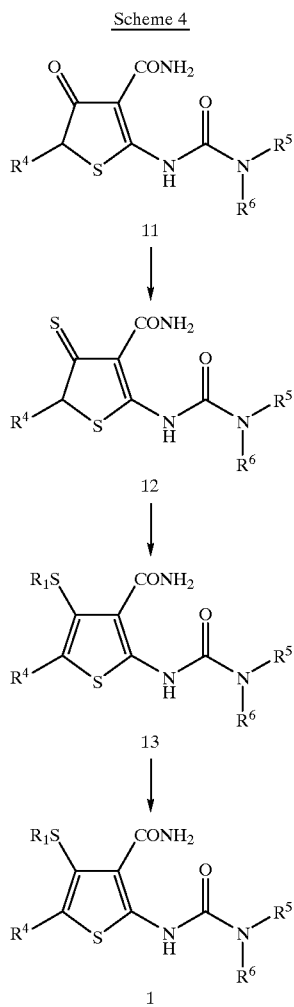

In Scheme 4, the thiophene 11 may be prepared by treatment of the thiophene 10 with a mixture of ammonium chloride and ammonium hydroxide (concentrated aqueous solution) in a sealed tube at 23 to 70° C. for a period of time sufficient to effect complete conversion of 10 to 11. The compound 11 is then treated with a suitable sulfur transfer reagent, preferably Lawesson's reagent in a nonpolar solvent, such as toluene at a temperature between 23° C. and 140° C. for a period of time sufficient to effect complete consumption of compound 10. The thiophene 11 is then treated with a suitable alkyl halide, such as an alkyl chloride, bromide or iodide, and a suitably strong base, such as a tertiary amine base, in a polar solvent, such as THF or DMF, preferably a 6:1 mixture of THF:DMF (N,N-dimethylforamide) for at a temperature of 0° C. to 100° C. for a period of time sufficient to effect complete consumption of 11. The compound of formula 1 is then isolated.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of formula 1 that are basic in nature are capable of forming a wide variety of different salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formula 1 that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formulas 1. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

Included in the present invention are compounds identical to the compounds of formula 1 but for the fact that one or more hydrogen or carbon atoms are replaced by isotopes thereof. Such compounds are useful as research and diagnostic tools in metabolism pharmokinetic studies and in binding assays. Specific applications in research include radioligand binding assays, autoradiography studies and in vivo binding studies. Included among the radiolabelled forms of the compounds of formula 1 are the tritium and $C^{14}$ isotopes thereof.

The in vitro activity of the compounds of formula 1 in inhibiting the KDR/VEGF receptor may be determined by the following procedure.

The ability of the compounds of the present invention to inhibit tyrosine kinase activity may be measured using a recombinant enzyme in an assay that measures the ability of compounds to inhibit the phosphorylation of the exogenous substrate, polyGluTyr (PGT, Sigma™, 4:1). The kinase domain of the human KDR/VEGF receptor (amino acids 805–1350) is expressed in Sf9 insect cells as a glutathione S-transferase (GST)-fusion protein using the baculovirus expression system. The protein is purified from the lysates of these cells using glutathione agarose affinity columns. The enzyme assay is performed in 96-well plates that are coated with the PGT substrate (0.625 μg PGT per well). Test compounds are diluted in dimethylsulfoxide (DMSO), and then added to the PGT plates so that the final concentration of DMSO in the assay is 1.6% (v/v). The recombinant enzyme is diluted in phosphorylation buffer (50 mM Hepes, pH 7.3, 125 mM NaCl, 24 mM $MgCl_2$). The reaction is initiated by the addition of ATP to a final concentration of 10 μM. After a 30 minute incubation at room temperature with shaking, the reaction is aspirated, and the plates are washed with wash buffer (PBS-containing 0.1% Tween-20). The amount of phosphorylated PGT is quantitated by incubation with a HRP-conjugated (HRP is horseradish peroxidase) PY-54 antibody (Transduction Labs), developed with TMB peroxidase (TMB is 3,3',5,5'-tetramethylbenzidine), and the reaction is quantitated on a BioRad™ Microplate reader at 450 nM. Inhibition of the kinase enzymatic activity by the test compound is detected as a reduced absorbance, and the concentration of the compound that is required to inhibit the signal by 50% is reported as the $IC_{50}$ value for the test compound.

To measure the ability of the compounds to inhibit KDR tyrosine kinase activity for the full length protein that exists in a cellular context, the porcine aortic endothelial (PAE) cells transfected with the human KDR (Waltenberger et al., J. Biol. Chem. 269:26988, 1994) may be used. Cells are plated and allowed to attach to 96-well dishes in the same media (Ham's F12) with 10% FBS (fetal bovine serum). The cells are then washed, re-fed with serum depleted media that contains 0.1% (v/v) bovine serum albumin (BSA), and allowed to incubate for 24 hours. Immediately prior to dosing with compound, the cells are re-fed with the serum depleted media (without BSA). Test compounds, dissolved in DMSO, are diluted into the media (final DMSO concentration 0.5% (v/v)). At the end of a 2 hour incubation, $VEGF_{165}$ (50 ng/ml final) is added to the media for an 8 minute incubation. The cells are washed and lysed in HNTG buffer (20 mM Hepes, pH 7.5, 150 mM NaCl, 0.2% Triton™ X-100, 10% glycerol, 0.2 mM PMSF (phenymethylsulfonyl fluoride), 1 μg/ml pepstatin, 1 μg/ml leupeptin, 1 μg/ml aprotonin, 2 mM sodium pyrophosphate, 2 mM sodium orthovanadate). The extent of phosphorylation of KDR is measured using an ELISA assay. The 96-well plates are coated with 1 μg per well of goat anti-rabbit antibody. Unbound antibody is washed off the plate and remaining sites are blocked with Superblock buffer (Pierce) prior to addition of the anti-flk-1 C-20 antibody (0.5 μg per plate, Santa Cruz). Any unbound antibody is washed off the plates prior to addition of the cell lysate. After a 2 hour incubation of the lysates with the flk-1 antibody, the KDR associated phosphotyrosine is quantitated by development with the HRP-conjugated PY-54 antibody and TMB, as described above. The ability of the compounds to inhibit the VEGF-stimulated autophosphorylation reaction by 50%, relative to VEGF-stimulated controls is reported as the $IC_{50}$ value for the test compound.

The ability of the compounds to inhibit mitogenesis in human endothelial cells is measured by their ability to inhibit $^3$H-thymidine incorporation into HUVE cells (human umbilical vein endothelial cells, Clonetics™). This assay has been well described in the literature (Waltenberger J et al. J. Biol. Chem. 269: 26988, 1994; Cao Y et al. J. Biol. Chem. 271: 3154, 1996). Briefly, $10^4$ cells are plated in collagen-coated 24-well plates and allowed to attach. Cells are re-fed in serum-free media, and 24 hours later are treated with various concentrations of compound (prepared in DMSO, final concentration of DMSO in the assay is 0.2% v/v), and 2–30 ng/ml $VEGF_{165}$. During the last 3 hours of the 24 hour compound treatment, the cells are pulsed with $^3$H thymidine (NEN, 1 μCi per well). The media are then removed, and the cells washed extensively with ice-cold Hank's balanced salt solution, and then 2 times with ice cold trichloroacetic acid (10% v/v). The cells are lysed by the addition of 0.2 ml of 0.1 N NaOH, and the lysates transferred into scintillation vials. The wells are then washed with 0.2 ml of 0.1 N HCl, and this wash is then transferred to the vials. The extent of $^3$H thymidine incorporation is measured by scintillation counting. The ability of the compounds to inhibit incorporation by 50%, relative to control (VEGF treatment with DMSO vehicle only) is reported as the $IC_{50}$ value for the test compound.

The activity of the compounds of formula 1, in vivo, can be determined by the amount of inhibition of tumor growth by a test compound relative to a control. The tumor growth inhibitory effects of various compounds are measured according to the methods of Corbett T. H., et al. "Tumor Induction Relationships in Development of Transplantable Cancers of the Colon in Mice for Chemotherapy Assays, with a Note on Carcinogen Structure", *Cancer Res.*, 35, 2434–2439 (1975) and Corbett, T. H., et al., "A Mouse Colon-tumor Model for Experimental Therapy", *Cancer Chemother. Rep. (Part 2)*", 5, 169–186 (1975), with slight modifications. Tumors are induced in the flank by s.c. injection of $1 \times 10^6$ log phase cultured tumor cells suspended in 0.1–0.2 ml PBS. After sufficient time has elapsed for the tumors to become palpable (5–6 mm in diameter), the test animals (athymic mice) are treated with active compound (formulated by dissolution in appropriate diluent, for example water or 5% Gelucire™ 44/14 m PBS by the intraperitoneal (ip) or oral (po) routes of administration once or twice daily for 5–10 consecutive days. In order to determine an anti-tumor effect, the tumor is measured in millimeters with Vernier calipers across two diameters and the tumor volume ($mm^3$) is calculated using the formula: Tumor weight=(length×[width]$^2$)/2, according to the methods of Geran, R. I., et al. "Protocols for Screening Chemical Agents and Natural Products Against Animal Tumors and Other Biological Systems", Third Edition, *Cancer Chemother. Rep.*, 3, 1–104 (1972). The flank site of tumor implantation provides reproducible dose/response effects for a variety of chemotherapeutic agents, and the method of measurement (tumor diameter) is a reliable method for assessing tumor growth rates.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration and the judgement of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumour substances, for example those selected from, for example, mitotic inhibitors, for example vinblastine; alkylating agents, for example cis-platin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations.

Preparation 1

2-(3,3-Dimethyl-ureido)-4-oxo-4,5-dihydro-thiophene-3-carboxylic acid methyl ester A solution of methyl 4-chloroacetoacetate (1.77 mL, 15.3 mmol) in THF (10 mL) was added to a 0 C suspension of sodium hydride (386 mg) in THF (40 mL). Stirring was continued until bubbling ceased to afford a light-yellow solution. Next was added a solution of N,N-dimethylaminoacylisothiocyanate (2.00 g, 15.4 mmol) in THF (10 mL). A light-yellow suspension formed after approximately one minute. The reaction was stirred overnight at ambient temperature. The mixture was next partitioned between water and an ethyl acetate/methylene chloride mixture. The organic layer was dried ($Na_2SO_4$), concentrated, and recrystallized from methanol to afford the title compound as a light-yellow solid (2.09 g, 8.56 mmol, 56%) $^1$H NMR ($CDCL_3$, 400 MHz) 3.10 (br. s, 6H), 3.56 (s, 2H), 3.86 (s, 3H), 12.41 (s, 1H).

2-(3,3-Dimethyl-ureido)-4-propoxy-thiophene-3-carboxylic acid methyl ester

A solution of 2-(3,3-Dimethyl-ureido)-4-oxo-4,5-dihydro-thiophene-3-carboxylic acid methyl ester (50 mg, 0.205 mmol) in n-propanol (5 mL) was treated with $H_2SO_4$ (5 microliters) and stirred at ambient temperature for 12 hours. Little reaction was observed so the temperature was increased to 100° C. Little reaction was observed after 2 hours so four angstrom seives were added and the reaction continued at 100° C. for two additional hours at which point sufficient product was observed. The mixture was then concentrated and the residue purified via radial chromatography on a 4 mm plate using hexanes/ethyl acetate (1/1) to afford the title compound as a white solid (31 mg, 0.108 mmol, 53%) $^1$H NMR ($CDCL_3$, 400 MHz) 1.03 (t, 3H, J=7.3 Hz), 1.78–1.84 (m, 2H), 3.06 (s, 6H), 3.84–3.89 (m, 5H), 5.51 (s, 1H), 11.08 (s, 1H).

EXAMPLE 1

2-(3,3-Dimethyl-ureido)-4-propoxy-thiophene-3-carboxylic acid amide

A solution of 2-(3,3-Dimethyl-ureido)-4-propoxy-thiophene-3-carboxylic acid methyl ester ( ) in ethanol (6 mL) was treated with concentrated ammonium hydroxide (6 mL) in a sealed tube and heated to 40° C. for 5 hours. The mixture was then cooled, evaporated, acidified with a small amount of acetic acid and purified via radial chromatography on a 2 mm plate using hexanes/ethyl acetate (3/1) plus 2% methanol as eluent to afford a white solid (15 mg, 55.3 micromol, 51%) $^1$H NMR ($CDCL_3$, 400 MHz) 1.03 (t, 3H, J=7.3 Hz), 1.81–1.88 (m, 2H), 3.04 (s, 6H), 3.97 (t, 2H, J=6.6 Hz), 5.33 (broad s, 1H), 5.55 (s, 1H), 7.50 (broad s, 1H), 12.00 (s, 1H).

What is claimed is:

1. A compound selected from the group consisting of:

2-(3,3-Dimethyl-ureido)-4-propoxy-thiophene-3-carboxylic acid amide;

4-Butoxy-2-(3,3-dimethyl-ureido)-thiophene-3-carboxylic acid amide;

2-(3,3-Dimethyl-ureido)-4-pentyloxy-thiophene-3-carboxylic acid amide;
2-(3,3-Dimethyl-ureido)-4-hexyloxy-thiophene-3-carboxylic acid amide;
2-(3,3-Dimethyl-ureido)4-heptyloxy-thiophene-3-carboxylic acid amide;
4-Benzylsulfanyl-2-(3,3-dimethyl-ureido)-thiophene-3-carboxylic acid amide;
2-(3,3-Dimethyl-ureido)-4-hexylsulfanyl-thiophene-3-carboxylic acid amide;
2-(3,3-Dimethyl-ureido)-4-pentylsulfanyl-thiophene-3-carboxylic acid amide;
2-(3,3-Dimethyl-ureido)-4-phenethylsulfanyl-thiophene-3-carboxylic acid amide;
2-(3,3-Dimethyl-ureido)-4-(pyridin-2-ylmethylsulfanyl)-thiophene-3-carboxylic acid amide;
2-(3,3-Dimethyl-ureido)-4-(naphthalen-1-ylmethylsulfanyl)-thiophene-3-carboxylic acid amide;
2-(3,3-Dimethyl-ureido)-4-(naphthalen-2-ylmethylsulfanyl)-thiophene-3-carboxylic acid amide;
2-(3,3-Dimethyl-ureido)-4-(quinolin-2-ylmethylsulfanyl)-thiophene-3-carboxylic acid amide
4-(4-Chloro-benzylsulfanyl)-2-(3,3-dimethyl-ureido)-thiophene-3-carboxylic acid amide;
2-(3,3-Dimethyl-ureido)-4-(1-phenyl-ethylsulfanyl)-thiophene-3-carboxylic acid amide
4-(2-Chloro-benzylsulfanyl)-2-(3,3-dimethyl-ureido)-thiophene-3-carboxylic acid amide
4-(3-Chloro-benzylsulfanyl)-2-(3,3-dimethyl-ureido)-thiophene-3-carboxylic acid amide
2-(3,3-Dimethyl-ureido)-4-(4-methyl-benzylsulfanyl)-thiophene-3-carboxylic acid amide;
2-(3,3-Dimethyl-ureido)-4-(4-methoxy-benzylsulfanyl)-thiophene-3-carboxylic acid amide;
2-(3,3-Dimethyl-ureido)-4-(4-vinyl-benzylsulfanyl)-thiophene-3-carboxylic acid amide;
2-(3,3-Dimethyl-ureido)-4-(4-trifluoromethyl-benzylsulfanyl)-thiophene-3-carboxylic acid amide;
2-(3,3-Dimethyl-ureido)-4-(pyridin-4-ylmethylsulfanyl)-thiophene-3-carboxylic acid amide;
2-(3,3-Dimethyl-ureido)-4-(pyridin-3-ylmethylsulfanyl)-thiophene-3-carboxylic acid amide;
5-Acetylamino-3-pentylsulfanyl-isothiazole-4-carboxylic acid amide;
5-Benzoylamino-3-pentylsulfanyl-isothiazole-4-carboxylic acid amide;
1-Methyl-3-[3-pentylsulfanyl-4-(1H-tetrazol-5-yl)-isothiazol-5-yl]-urea;
5-(3-Methyl-ureido)-3-pentylsulfanyl-isothiazole-4-carboxylic acid.

2. A pharmaceutical composition which comprises a therapeutically effective amount of a compound of claim 1, or a pharmaceutically acceptable salt or hydrate thereof, and a pharmaceutically acceptable carrier.

* * * * *